US012692237B2

(12) United States Patent
Dzwiniel et al.

(10) Patent No.: US 12,692,237 B2
(45) Date of Patent: Jul. 28, 2026

(54) CONTINUOUS METHOD FOR PREPARING TRICYANOIMIDAZOLE

(71) Applicant: UCHICAGO ARGONNE, LLC, Chcago, IL (US)

(72) Inventors: Trevor L. Dzwiniel, Carol Stream, IL (US); Krzysztof Z. Pupek, Plainfield, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 305 days.

(21) Appl. No.: 18/206,316

(22) Filed: Jun. 6, 2023

(65) Prior Publication Data

US 2023/0406828 A1 Dec. 21, 2023

Related U.S. Application Data

(60) Provisional application No. 63/354,168, filed on Jun. 21, 2022.

(51) Int. Cl.
*C07D 233/90* (2006.01)

(52) U.S. Cl.
CPC .................................. *C07D 233/90* (2013.01)

(58) Field of Classification Search
CPC .................................................... C07D 233/90
See application file for complete search history.

(56) References Cited

U.S. PATENT DOCUMENTS 3,882,140 A 5/1975 Webster

FOREIGN PATENT DOCUMENTS

WO WO-2016/203390 A1 12/2016

OTHER PUBLICATIONS

Allan, S., et al., "Electron Donors and Cyanoimidazole Acceptors: Cyclic Voltammetry and Molecular Orbital Study," Synthetic Metals, 25 (1988), pp. 139-155.

Aspen, P.G., et al., "Nucleophilic aromatic substitution in 4,5-Dicyanoimidazoles," Heterocycles, vol. 29, No. 7, 1989, pp. 1325-1329.

Barral, K., et al., "Efficient Conversion of Aromatic Amines into Azides: A One-Pot Synthesis of Triazole Linkages," Organic Letters, 2007, vol. 9, No. 9, pp. 1809-1811.

Coad, E.C., et al., "Synthesis, Characterization, and Thermolysis of C15N12," J. Org. Chem. 1996, 61, pp. 6666-6672.

D'Attoma, J., et al., "Efficient Transposition of the Sandmeyer Reaction from Batch to Continuous Process," Org. Process Res. Dev. 2017, 21, pp. 44-51.

Park, N.H., et al., "Rapid Synthesis of Aryl Fluorides in Continuous Flow through the Balz-Schiemann Reaction," Angew. Chem. 2016, 128 (12086-12090.

Schafer, G., et al., "Development of a Scalable Route for a Key Thiadiazole Building Block via Sequential Sandmeyer Bromination and Room-Temperature Suzuki-Miyaura Coupling," Org. Process Res. Dev. 2020, 24, pp. 228-234.

Sheppard, W.A, et al., "Hydrogen Cyanide Chemistry. V. Diazodicyanoimidazole and Dicyanoimidazole Halonium Ylides", J. Org. Chem. 31, 4097, 1966, pp. 2695-2697.

Yu, Z., et al., "A Fully Continuous-Flow Process for the Synthesis of p-Cresol: Impurity Analysis and Process Optimization," Org. Process Res. Dev. 2017, 21, pp. 1644-1652.

*Primary Examiner* — Shawquia Jackson
(74) *Attorney, Agent, or Firm* — Foley & Lardner LLP

(57) ABSTRACT

Disclosed herein are methods and continuous processes of preparing tricyanoimidazole (a compound of Formula (A)) or a salt (e.g., a potassium or lithium salt) thereof. The methods include (a) contacting a first reaction stream comprising a compound of Formula (I)

(I)

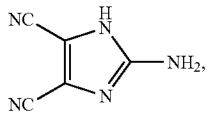

with a second reaction stream comprising a nitrite source, to form a first combined reaction stream comprising a compound of Formula (II)

(II)

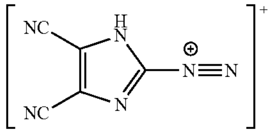

or a tautomer thereof, wherein the first combined reaction stream flows through a continuous flow reactor at a flow rate providing a residence time sufficient for converting a compound of Formula (I) to a compound of Formula (II); and (b) a step selected from step (b1) and (b2), wherein step (b1) comprises contacting the first combined reaction stream with a third reaction stream comprising a cyanide source to form a second combined reaction stream to form a compound of Formula (A) or a salt thereof, wherein the second combined reaction stream is allowed to flow through a continuous flow reactor; and step (b2) comprises quenching the reactor effluent exiting from the continuous flow reactor with a cyanide source to form a quench mixture comprising compound of Formula (A) or a salt thereof.

20 Claims, 1 Drawing Sheet

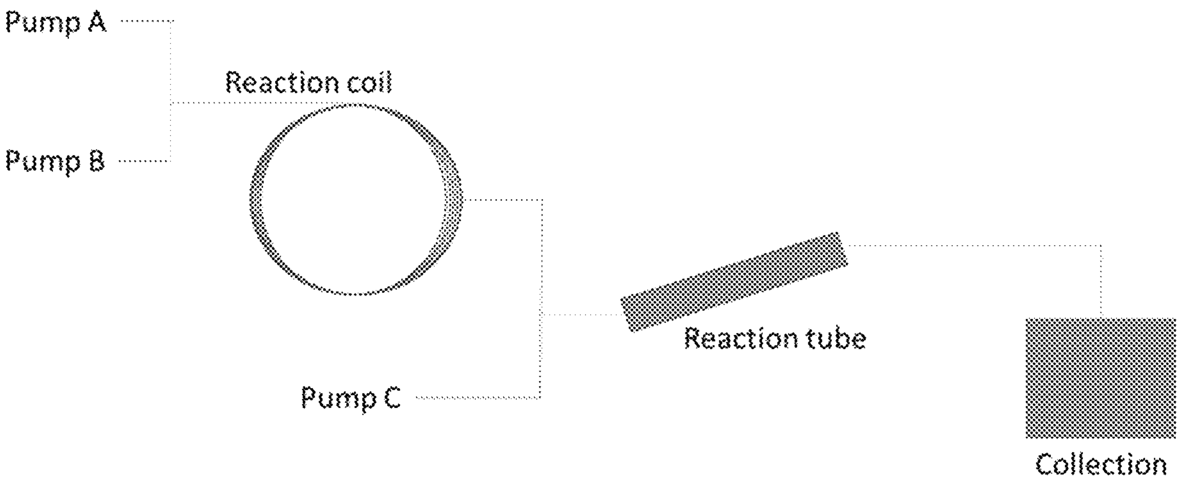
Pump A
Reaction coil
Pump B
Pump C
Reaction tube
Collection

CONTINUOUS METHOD FOR PREPARING TRICYANOIMIDAZOLE

CROSS-REFERENCE TO RELATED APPLICATIONS

This application claims priority to and the benefit of U.S. Provisional Patent Application No. 63/354,168, filed Jun. 21, 2022, the contents of which are incorporated by reference in their entirety.

STATEMENT OF GOVERNMENT INTEREST

This invention was made with government support under Contract No. DE-AC02-06CH 11357 awarded by the U.S. Department of Energy. The government has certain rights in the invention.

TECHNICAL FIELD

The present disclosure relates generally to methods for preparing tricyanoimidazole compounds, which are useful, e.g., as electrolytes for electrochemical cells and batteries.

BACKGROUND

Lithium tricyanoimidazolide is a new lithium salt useful as an electrolyte for lithium batteries. For example, a tricyanoimidazolide salt can be non-corrosive, and more stable than a hexafluorophosphate salt, and thus would be able to prevent anodic dissolution. In addition, a tricyanoimidazolide salt may have synergistic effect when used with other salts, enabling high voltage use of Li-FSI (lithium bis (fluorosulfonyl)imide).

While methods for synthesis of tricyanoimidazole have been described, there remains a need for new and safe methods to manufacture tricyanoimidazole (and/or a lithium salt thereof) with improved overall yield and reduced costs. Continuous flow chemistry (CFC) is an emerging technology with desirable features compared to conventional batch manufacturing processes. Accordingly, described herein are continuous methods of manufacturing tricyanoimidazole compounds or a salt (e.g., a lithium and/or potassium salt) thereof.

SUMMARY OF THE INVENTION

The present invention is based, in part, on the surprising discovery that tricyanoimidazole (or a salt thereof) can be manufactured using the methods and compositions described herein.

In one aspect, disclosed herein is a continuous process for preparing a compound of Formula (A)

(A)

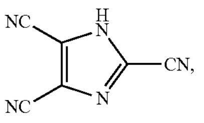

or a salt thereof, comprising:

(a) contacting a first reaction stream comprising a compound of Formula (I)

(I)

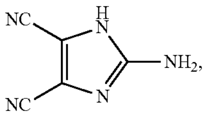

with a second reaction stream comprising a nitrite source, to form a first combined reaction stream comprising a compound of Formula (II)

(II)

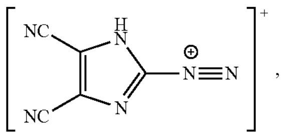

or a tautomer thereof, wherein the first combined reaction stream flows through a continuous flow reactor at a flow rate providing a residence time sufficient for converting a compound of Formula (I) to a compound of Formula (II); and (b) a step selected from step (b1) and (b2), wherein step (b1) comprises contacting the first combined reaction stream with a third reaction stream comprising a cyanide source to form a second combined reaction stream to form a compound of Formula (A) or a salt thereof, wherein the second combined reaction stream is allowed to flow through a continuous flow reactor; and step (b2) comprises quenching the reactor effluent exiting from the continuous flow reactor with a cyanide source to form a quench mixture comprising compound of Formula (A) or a salt thereof.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

FIG. 1 schematically illustrates one embodiment of a continuous flow reactor system.

DETAILED DESCRIPTION

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

All temperatures are in degrees Celsius (° C.) unless otherwise specified. Purity and related numeric values (%) are as measured by HPLC, unless otherwise specified.

Isolated: As used herein, the term “isolated” refers to a substance and/or entity that has been (1) separated from at least some of the components with which it was associated when initially produced (whether in nature and/or in an experimental setting), and/or (2) produced, prepared, and/or manufactured by the hand of man. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free (e.g., contains less than 5 wt %, 4 wt %, 3 wt %, 2 wt %, or 1 wt %) of other components. As used herein, calculation of percent purity of isolated substances and/or entities should not include excipients (e.g., buffer, solvent, water, etc.).

Approximately or about: As used herein, the term "approximately" or "about", as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used in the description and the appended claims, the singular forms "a", "an", and "the" include plural referents unless the context clearly dictates otherwise. Thus, for example, reference to "a composition" includes mixtures of two or more such compositions.

Throughout the description and claims of this specification the word "comprise" and other forms of the word, such as "comprising" and "comprises", means including but not limited to, and is not intended to exclude, for example, other additives, components, integers, or steps.

"Optional" or "optionally" means that the subsequently described event or circumstance may or may not occur, and that the description includes instances where the event or circumstance occurs and instances where it does not.

Tautomer: refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH.

Solvate: can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

Salt: as used herein, a salt refers to preferably a salt of a mineral acid, or an organic acid such as a carboxylic acid or a sulfonic acid, and/or to alkali, alkaline earth, and various ammonium (including tetraalkyl ammonium, pyridinum, imidazolium and the like) salts.

Solvent: can include, but is not limited to, non-polar, polar aprotic, and polar protic solvents. Illustrative examples of non-polar solvents include, but are not limited to, pentane, cyclopentane, hexane, cyclohexane, benzene, toluene, xylene, 1,4-dioxane, chloroform, diethyl ether, and dichloromethane (DCM). Illustrative examples of polar aprotic solvents include, but are not limited to, tetrahydrofuran (TRF), ethyl acetate, isopropyl acetate (IPAc), acetone, dimethylformamide (DMF), dimethyl acetamide (DMAc), acetonitrile (MeCN), butyronitrile, dimethyl sulfoxide (DMSO), nitromethane, and propylene carbonate. Illustrative examples of polar protic solvents include, but are not limited to, formic acid, n-butanol, isopropanol (IPA), n-propanol, ethanol, methanol, acetic acid, and water.

Acid: refers to molecules or ions capable of donating a hydrogen (proton or hydrogen ion $H^+$), or, alternatively, capable of forming a covalent bond with an electron pair (e.g., a Lewis acid). Acids can include, but is not limited to, mineral acids, sulfonic acids, carboxylic acids, halogenated carboxylic acids, and vinylogous carboxylic acids.

Base: as used herein, "base" refers to a compound that can accept a proton or donate a lone electron pair. Examples of bases include, alkali ($OH^-$), carbonate, bicarbonate, alkoxides (alkyl-O($^-$)), hydrides (alkali metal hydrides and $CaH_2$), amides, and neutral nitrogen containing bases such as $R_3N$, where in R is alkyl, pyridine, and the like.

Methods of the Invention

Disclosed herein are continuous (including semi-continuous) methods and processes of preparing tricyanoimidazole (a compound of Formula (A)) or a salt thereof (e.g., a compound of Formula (B)). An exemplary FIGURE illustrating a continuous flow reactor system that may be used in the described process is shown in FIG. 1. For example, pump A may be used to inject the first reaction stream (or the second reaction stream) described herein; pump B may be used to inject the second reaction stream (or the first reaction stream) described herein; and pump C may be used to inject the third reaction stream described herein.

In certain embodiments, the processes disclosed herein can take place concurrently, in a sequential order as described herein, or in any possible order thereof. In any embodiments, the process is a full continuous method (e.g., full flow chemistry route). In any embodiments, the process is a semi-continuous method (e.g., semi-flow chemistry route).

In certain embodiments, the processes disclosed herein can take place at atmospheric pressure. In certain embodiments, the processes disclosed herein can take place at an elevated pressure. In any embodiments, the processes disclosed herein takes place at a pressure of about 1 to 10 bar. In any embodiments, the processes disclosed herein takes place at a pressure of at least about 1 to 10 bar. In any embodiments, the processes disclosed herein takes place at a pressure of no more than about 1 to 10 bar. In any embodiments, the processes disclosed herein takes place at a pressure of about 1-10, 1-8, 1-6, or 1-4 bar. In any embodiments, the processes disclosed herein takes place at a pressure of about 1, 2, 3, 4, 5, 6, 7, 8, 9, or 10 bar or a range between and including any two of the foregoing values.

Step (a)

In any embodiments, methods described herein may include a step (a). In any embodiments, a compound of Formula (II) can be prepared according to Scheme 1.

Scheme 1 Exemplary Step (a)

i.

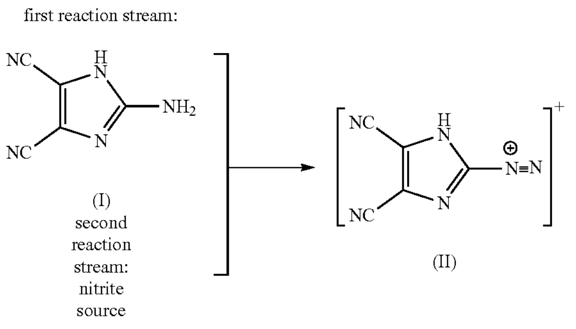

ii.

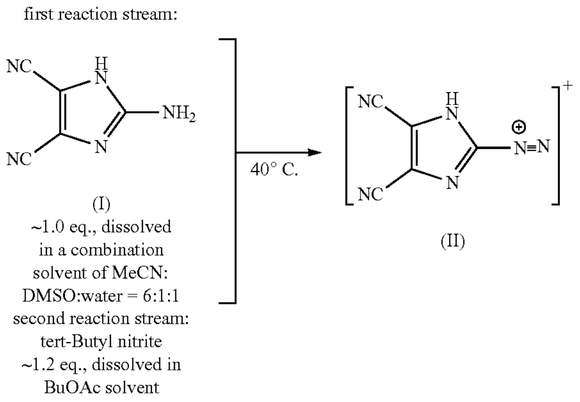

As shown in Scheme 1-i, a step (a) can comprise contacting a first reaction stream comprising a compound of Formula (I) with a second reaction stream comprising a nitrite source, to form a first combined reaction stream comprising a compound of Formula (II) or a tautomer thereof. A further exemplary embodiment of a step (a) is shown in Scheme 1-ii.

In any embodiments, the reaction stream (e.g., the first combined reaction stream) is allowed to flow through a continuous flow reactor at a flow rate providing a residence time sufficient for converting a compound of Formula (I) to a compound of Formula (II). In any embodiments, the reaction stream (e.g., the first combined reaction stream) is allowed to flow through a continuous flow reactor at a flow rate providing a residence time in the range of about 5 minutes to about 24 hours. In any embodiments, the reaction stream (e.g., the first combined reaction stream) is allowed to flow through a continuous flow reactor at a flow rate providing a residence time of at least about 5 minutes to about 24 hours. In any embodiments, the reaction stream (e.g., the first combined reaction stream) is allowed to flow through a continuous flow reactor at a flow rate providing a residence time of no more than about 5 minutes to about 24 hours.

In any embodiments, the reaction stream (e.g., the first combined reaction stream) is allowed to flow through a continuous flow reactor at a flow rate providing a residence time in the range of about 5 minutes to about 24 hours, about 5 minutes to about 20 hours, about 5 minutes to about 15 hours, about 5 minutes to about 10 hours, about 5 minutes to about 5 hours, about 5 minutes to about 1 hour, about 5 minutes to about 50 minutes, about 5 minutes to about 40 minutes, about 5 minutes to about 30 minutes, about 5 minutes to about 25 minutes, about 5 minutes to about 20 minutes, about 5 minutes to about 15 minutes, or about 5 minutes to about 10 minutes. In any embodiments, the reaction stream (e.g., the first combined reaction stream) is allowed to flow through a continuous flow reactor at a flow rate providing a residence time in the range of about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 25 minutes, about 30 minutes, about 1 hour, about 2 hours, about 3 hours, about 4 hours, about 5 hours, about 10 hours, about 15 hours, about 20 hours, about 24 hours, or a range of times between and including any two of the foregoing times. In any embodiments, the reaction stream (e.g., the first combined reaction stream) is allowed to flow through a continuous flow reactor at a flow rate providing a residence time in the range of about 5 to 7 minutes.

In any embodiments, step (a) comprises a nitrite source. Exemplary nitrite source includes, but is not limited to tert-butyl nitrite, amyl nitrite, sodium nitrite, and nitrous acid. In any embodiments, a nitrite source is tert-butyl nitrite.

In any embodiments, a nitrite source is present in the first combined reaction stream in an amount of about 70 to 150 mol % relative to the compound of Formula (I). In any embodiments, a nitrite source is present in the first combined reaction stream in an amount of at least about 70 to 150 mol % relative to the compound of Formula (I). In any embodiments, a nitrite source is present in the first combined reaction stream in an amount of no more than about 70 to 150 mol % relative to the compound of Formula (I). In any embodiments, a nitrite source is present in the first combined reaction stream in an amount of about 70 to 150 mol %, about 70 to 140 mol %, about 70 to 130 mol %, about 70 to 120 mol %, about 80 to 120 mol %, or about 90 to 120 mol %, relative to the compound of Formula (I). In any embodiments, a nitrite source is present in the first combined reaction stream in an amount of about 70 mol %, about 75 mol %, about 80 mol %, about 85 mol %, about 90 mol %, about 95 mol %, about 100 mol %, about 105 mol %, about 110 mol %, about 115 mol %, about 120 mol %, about 125 mol %, about 130 mol %, about 135 mol %, about 140 mol %, about 145 mol %, or about 150 mol %, relative to the compound of Formula (I). In any embodiments, a nitrite source is present in the first combined reaction stream in an amount of about 120 mol % relative to the compound of Formula (I).

In any embodiments, the first reaction stream in step (a) comprises a solvent. In any embodiments, the second reaction stream in step (a) comprises a solvent. Exemplary solvents include but are not limited to, DMSO, Diglyme, MeCN, $H_2O$, DMF, NMP, BuOAc, and any combination of two or more thereof.

In any embodiments, the first reaction stream in step (a) comprises a solvent that is a combination of MeCN, DMSO, and water. In any embodiments, MeCN is present in the combination solvent (e.g., a combination of MeCN, DMSO, and water) in an amount of about 30% to 80% (e.g., v/v percent). In any embodiments, MeCN is present in the combination solvent (e.g., a combination of MeCN, DMSO, and water) in an amount of at least about 30% to 80% (e.g., v/v percent). In any embodiments, MeCN is present in the combination solvent (e.g., a combination of MeCN, DMSO, and water) in an amount of no more than about 30% to 80% (e.g., v/v percent). In any embodiments, MeCN is present in the combination solvent (e.g., a combination of MeCN, DMSO, and water) in an amount of about 30% to 80%, about 40% to 80%, about 50% to 80%, about 60% to 80%, or about 70% to 80% (e.g., v/v percent). In any embodiments, MeCN is present in the combination solvent (e.g., a combination of MeCN, DMSO, and water) in an amount of about 30%, about 40%, about 50%, about 60%, about 65%, about 70%, about 75%, or about 80% (e.g., v/v percent).

In any embodiments, DMSO is present in the combination solvent (e.g., a combination of MeCN, DMSO, and water) in an amount of about 10% to 30% (e.g., v/v percent). In any embodiments, DMSO is present in the combination solvent (e.g., a combination of MeCN, DMSO, and water) in an amount of at least about 10% to 30% (e.g., v/v percent). In any embodiments, DMSO is present in the combination solvent (e.g., a combination of MeCN, DMSO, and water) in an amount of no more than about 10% to 30% (e.g., v/v percent). In any embodiments, DMSO is present in the combination solvent (e.g., a combination of MeCN, DMSO, and water) in an amount of about 10% to 30%, about 10% to 25%, about 10% to 20%, or about 10% to 15% (e.g., v/v percent). In any embodiments, DMSO is present in the combination solvent (e.g., a combination of MeCN, DMSO, and water) in an amount of about 10%, about 15%, about 20%, about 25%, or about 30% (e.g., v/v percent).

In any embodiments, water is present in the combination solvent (e.g., a combination of MeCN, DMSO, and water) in an amount of about 10% to about 30% (e.g., v/v percent). In any embodiments, water is present in the combination solvent (e.g., a combination of MeCN, DMSO, and water) in an amount of at least about 10% to about 30% (e.g., v/v percent). In any embodiments, water is present in the combination solvent (e.g., a combination of MeCN, DMSO, and water) in an amount of no more than about 10% to about 30% (e.g., v/v percent). In any embodiments, water is present in the combination solvent (e.g., a combination of MeCN, DMSO, and water) in an amount of about 10% to 30%, about 10% to 25%, about 10% to 20%, or about 10% to 15% (e.g., v/v percent). In any embodiments, water is present in the combination solvent (e.g., a combination of MeCN, DMSO, and water) in an amount of about 10%, about 15%, about 20%, about 25%, or about 30% (e.g., v/v percent).

In any embodiments, the first reaction stream in step (a) comprises a solvent that is a combination of MeCN, DMSO, and water, and wherein MeCN:DMSO:water=6:1:1 (e.g., v/v percent).

In any embodiments, the second reaction stream in step (a) comprises a solvent that is BuOAc.

In any embodiments, step (a) occur at a temperature of about 20° C. to 45° C. In any embodiments, step (a) occur at a temperature of at least about 20° C. to 45° C. In any embodiments, step (a) occur at a temperature of no more than about 20° C. to 45° C. In any embodiments, step (a) occur at a temperature of about 20° C. to 45° C., about 30° C. to 45° C., or about 35° C. to 45° C. In any embodiments, step (a) occur at a temperature of about 20° C., about ° C., about 30° C., about 35° C., about 40° C., or about 45° C. In any embodiments, step (a) occur at a temperature of about 40° C. or about 45° C.

In any embodiments, the first combined reaction stream may be biphasic (or multi-phasic). In any embodiments, the process described herein may optionally include step (c*): a continuous separation of the biphasic (or multi-phasic) reaction stream before next step (e.g., step (b)).

Step (b)

In any embodiments, methods described herein may include a step (b). In any embodiments, the process described herein is a full continuous method, and step (b) is step (b1), wherein step (b1) is a continuous synthesis. In any embodiments, the process described herein is a semi-continuous method, and step (b) is step (b2), wherein step (b2) is a batch synthesis.

In any embodiments, a compound of Formula (A) can be prepared according to step (b) (step (b1) and/or step (b2)). In any embodiments, a salt (e.g., a potassium salt) of the compound of Formula (A) is formed from step (b) (step (b1) and/or step (b2)).

Scheme 2 Exemplary Step (b)

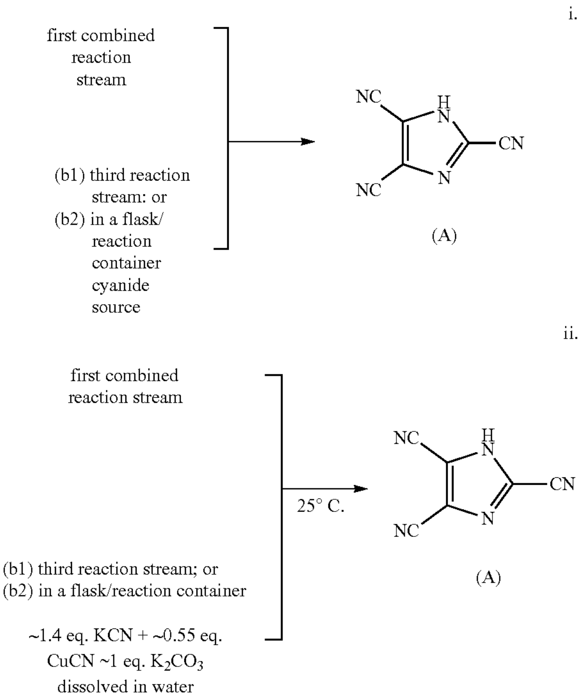

As shown in Scheme 2-i, a step (b) can be step (b1), which comprises contacting the first combined reaction stream with a third reaction stream comprising a cyanide source to form a second combined reaction stream comprising a compound of Formula (A) or a salt (e.g., a potassium salt) thereof, wherein the second combined reaction stream is allowed to flow through a continuous flow reactor. Alternatively, a step (b) can be step (b2), which comprises quenching the reactor effluent exiting from the continuous flow reactor with a cyanide source to form a quench mixture comprising a compound of Formula (A) or a salt (e.g., a potassium salt) thereof. A further exemplary embodiment of a step (b) (e.g., step (b1) and/or step (b2)) is shown in Scheme 2-ii.

In any embodiments, the reaction stream (e.g., the second combined reaction stream) is allowed to flow through a continuous flow reactor at a flow rate providing a residence time sufficient for converting a compound of Formula (II) to a compound of Formula (A) or a salt (e.g., a potassium salt) thereof. In any embodiments, the reaction stream (e.g., the second combined reaction stream) is allowed to flow through a continuous flow reactor at a flow rate providing a residence time in the range of about 5 minutes to about 24 hours. In any embodiments, the reaction stream (e.g., the second combined reaction stream) is allowed to flow through a continuous flow reactor at a flow rate providing a residence time of at least about 5 minutes to about 24 hours. In any embodiments, the reaction stream (e.g., the second combined reaction stream) is allowed to flow through a continuous flow reactor at a flow rate providing a residence time of no more than about 5 minutes to about 24 hours.

In any embodiments, the reaction stream (e.g., the second combined reaction stream) is allowed to flow through a continuous flow reactor at a flow rate providing a residence time in the range of about 5 minutes to about 24 hours, about 5 minutes to about 20 hours, about 5 minutes to about 15 hours, about 5 minutes to about 10 hours, about 5 minutes to about 5 hours, about 5 minutes to about 1 hour, about 5 minutes to about 50 minutes, about 5 minutes to about 40 minutes, about 5 minutes to about 30 minutes, about 5 minutes to about 25 minutes, about 5 minutes to about 20 minutes, about 5 minutes to about 15 minutes, or about 5 minutes to about 10 minutes. In any embodiments, the reaction stream (e.g., the second combined reaction stream) is allowed to flow through a continuous flow reactor at a flow rate providing a residence time in the range of about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 25 minutes, about 30 minutes, about 1 hour, about 2 hours, about 3 hours, about 4 hours, about 5 hours, about 10 hours, about 15 hours, about 20 hours, about 24 hours, or a range of times between and including any two of the foregoing times.

In any embodiments, a cyanide source is an inorganic cyanide salt. Exemplary cyanide source includes but is not limited to CuCN, KCN, NaCN, $Zn(CN)_2$, and any combination of two or more thereof. In any embodiments, a cyanide source is a combination of CuCN and KCN.

In any embodiments, the cyanide source (e.g., a combination of CuCN and KCN) is present in the second combined reaction stream or the quench mixture in an amount of about 100 to 300 mol % relative to the compound of Formula (II). In any embodiments, the cyanide source (e.g., a combination of CuCN and KCN) is present in the second combined reaction stream or the quench mixture in an amount of at least about 100 to 300 mol % relative to the compound of Formula (II). In any embodiments, the cyanide source (e.g., a combination of CuCN and KCN) is present in the second combined reaction stream or the quench mixture in an amount of no more than about 100 to 300 mol % relative to the compound of Formula (II). In any embodiments, the cyanide source (e.g., a combination of CuCN and KCN) is present in the second combined reaction stream or the quench mixture in an amount of about 100 to 300 mol %, about 100 to 250 mol %, about 100 to 200 mol %, or about 100 to 150 mol %, relative to the compound of Formula (II). In any embodiments, the cyanide source (e.g., a combination of CuCN and KCN) is present in the second combined reaction stream or the quench mixture in an amount of about 100 mol %, about 120 mol %, about 140 mol %, about 160 mol %, about 180 mol %, about 200 mol %, about 220 mol %, about 240 mol %, about 260 mol %, or about 300 mol %, relative to the compound of Formula (II). In any embodiments, the amount of compound of Formula (II) is assumed to be identical to the initial amount of compound of Formula (I).

In any embodiments, a cyanide source is a combination of CuCN and KCN, and wherein KCN is present in the second combined reaction stream or the quench mixture in an amount of about 50 to 200 mol % relative to the compound of Formula (II). In any embodiments, a cyanide source is a combination of CuCN and KCN, and wherein KCN is present in the second combined reaction stream or the quench mixture in an amount of at least about 50 to 200 mol % relative to the compound of Formula (II). In any embodiments, a cyanide source is a combination of CuCN and KCN, and wherein KCN is present in the second combined reaction stream or the quench mixture in an amount of no more than about 50 to 200 mol % relative to the compound of Formula (II). In any embodiments, a cyanide source is a combination of CuCN and KCN, and wherein KCN is present in the second combined reaction stream or the quench mixture in an amount of about 50 to 200 mol %, about 50 to 150 mol %, or about 100 to 150 mol %, relative to the compound of Formula (II). In any embodiments, a cyanide source is a combination of CuCN and KCN, and wherein KCN is present in the second combined reaction stream or the quench mixture in an amount of about 50 mol %, about 60 mol %, about 70 mol %, about 80 mol %, about mol %, about 100 mol %, about 110 mol %, about 120 mol %, about 130 mol %, about 140 mol %, about 150 mol %, about 160 mol %, about 170 mol %, about 180 mol %, about 190 mol %, or about 200 mol %, relative to the compound of Formula (II). In any embodiments, a cyanide source is a combination of CuCN and KCN, and wherein KCN is present in the second combined reaction stream or the quench mixture in an amount of about 140 mol % relative to the compound of Formula (II). In any embodiments, the amount of compound of Formula (II) is assumed to be identical to the initial amount of compound of Formula (I).

In any embodiments, a cyanide source is a combination of CuCN and KCN, and wherein CuCN is present in the second combined reaction stream or the quench mixture in an amount of about 20 to 100 mol % relative to the compound of Formula (II). In any embodiments, a cyanide source is a combination of CuCN and KCN, and wherein CuCN is present in the second combined reaction stream or the quench mixture in an amount of at least about 20 to 100 mol % relative to the compound of Formula (II). In any embodiments, a cyanide source is a combination of CuCN and KCN, and wherein CuCN is present in second combined reaction stream or the quench mixture in an amount of no more than about 20 to 100 mol % relative to the compound of Formula (II). In any embodiments, a cyanide source is a combination of CuCN and KCN, and wherein CuCN is present in the second combined reaction stream or the quench mixture in an amount of about 20 to 100 mol %, about 20 to 80 mol %, about 20 to 60 mol %, or about 40 to 60 mol %, relative to the compound of Formula (II). In any embodiments, a cyanide source is a combination of CuCN and KCN, and wherein CuCN is present in the second combined reaction stream or the quench mixture in an amount of about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about mol %, about 95 mol %, or about 100 mol %, relative to the compound of Formula (II). In any embodiments, a cyanide source is a combination of CuCN and KCN, and wherein CuCN is present in the second combined reaction stream or the quench mixture in an amount of about 55 mol % relative to the compound of Formula (II). In any embodiments, the amount of compound of Formula (II) is assumed to be identical to the initial amount of compound of Formula (I).

In any embodiments, step (b) (e.g., step (b1) and/or step (b2)) further comprises a base, i.e., the second combined reaction stream in step (b1) or the quench mixture in step (b2) further comprise a base. In any embodiments, the base is an inorganic base. In any embodiments, the base is a non-nucleophilic organic base (e.g., a tertiary amine). Exemplary inorganic bases include but are not limited to LiOH, NaOH, KOH, CsOH, $Li_2CO_3$, $Na_2CO_3$, $K_2CO_3$, $Cs_2CO_3$, $NaHCO_3$, $KHCO_3$, $CsHCO_3$, and any combination of two or more thereof. In any embodiments, the base is $K_2CO_3$.

In any embodiments, a base (e.g., $K_2CO_3$) is present in the second combined reaction stream or the quench mixture in an amount of about 100 to 300 mol % relative to the compound of Formula (II). In any embodiments, the base (e.g., $K_2CO_3$) is present in the second combined reaction stream or the quench mixture in an amount of at least about 100 to 300 mol % relative to the compound of Formula (II). In any embodiments, the base (e.g., $K_2CO_3$) is present in the second combined reaction stream or the quench mixture in an amount of no more than about 100 to 300 mol % relative to the compound of Formula (II). In any embodiments, the base (e.g., $K_2CO_3$) is present in the second combined reaction stream or the quench mixture in an amount of about 100 to 300 mol %, about 100 to 250 mol %, about 100 to 200 mol %, or about 100 to 150 mol %, relative to the compound of Formula (II). In any embodiments, the base (e.g., $K_2CO_3$) is present in the second combined reaction stream or the quench mixture in an amount of about 100 mol %, about 150 mol %, about 200 mol %, about 250 mol %, or about 300 mol %, relative to the compound of Formula (II). In any embodiments, the base (e.g., $K_2CO_3$) is present in the second combined reaction stream or the quench mixture in an amount of about 100 mol % relative to the compound of Formula (II). In any embodiments, the amount of compound of Formula (II) is assumed to be identical to the initial amount of compound of Formula (I).

In any embodiments, the cyanide source (e.g., a combination of CuCN and KCN) and/or the base (e.g., $K_2CO_3$) are dissolved in a solvent prior to step (b) (e.g., step (b1) and/or step (b2)). In any embodiments, a solvent is water. In any embodiments, step (b) is step (b1), and the third reaction stream comprises an aqueous solution comprising the cyanide source (e.g., a combination of CuCN and KCN) and the base (e.g., $K_2CO_3$). In any embodiments, step (b) is step (b2), and the first combined reaction stream (which is also the reactor effluent exiting from the continuous flow reactor) is quenched by an aqueous solution comprising the cyanide source (e.g., a combination of CuCN and KCN) and the base (e.g., $K_2CO_3$).

In any embodiments, step (b) (e.g., step (b1) and/or step (b2)) occurs at a temperature of about 20° C. to about 45° C. In any embodiments, step (b) (e.g., step (b1) and/or step (b2)) occur at a temperature of at least about 20° C. to 45° C. In any embodiments, step (b) (e.g., step (b1) and/or step (b2)) occur at a temperature of no more than about 20° C. to 45° C. In any embodiments, step (b) (e.g., step (b1) and/or step (b2)) occur at a temperature of about 20° C. to about 45° C., about 30° C. to about 45° C., or about 35° C. to about 45° C. In any embodiments, step (b) (e.g., step (b1) and/or step (b2)) occur at a temperature of about 20° C., about 25° C., about 30° C., about 35° C., about 40° C., about 45° C. or at a range between and including any two of the foregoing temperature values. In any embodiments, step (b) (e.g., step (b1) and/or step (b2)) occur at a temperature of about 25° C. In any embodiments, step (b1) occur at a temperature of about 25° C. In any embodiments, step (b2) occur at a temperature of about 25° C.

In any embodiments, the process described herein is a full continuous method, and step (b) is step (b1). In any embodiments, the first combined reaction stream, and/or the second combined reaction steam may be biphasic. In any embodiments, the process described herein may optionally include step (c*): a continuous separation of the biphase for one or more of the combined reaction streams. In any embodiments, the first combined reaction stream, and/or the second combined reaction stream may be multi-phasic, wherein each multiphasic stream consists of an organic-water phase and an immiscible organic solvent. In any embodiments, the process described herein may optionally include step (c*): a continuous separation of the multi-phase stream for one or more of the combined reaction streams. Exemplary immiscible organic solvents include but are not limited to butyl acetate, MTBE(methyl tert-butyl ether), toluene, dichloromethane, chloroform, heptane, TFT (trifluorotoluene), MeCN, and any combination thereof.

In any embodiments, the process described herein is a semi-continuous method, and step (b) is step (b2). In any embodiments, the reactor effluent exiting from the continuous flow reactor (e.g., the first combined reaction stream) is quenched with a dual-phase bulk cyanide source as described herein. (e.g., an aqueous solution comprising CuCN, KCN and $K_2CO_3$).

Steps (c) and (d)

In any embodiments, the process described herein may include collecting a reactor effluent exiting from the continuous flow reactor. In any embodiments, the process is a full continuous method, and a reactor effluent may be collected after step (b1) or step (c*). In any embodiments, the process is a semi-continuous method, and a reactor effluent may be collected after step (a).

In any embodiments, the process described herein may include a step (c), wherein the reaction mixture from step (b) (step (b1) and/or step (b2)) or step (c*) is extracted with an organic solvent. Exemplary organic solvents include but are not limited to butyl acetate, MTBE(methyl tert-butyl ether), toluene, dichloromethane, chloroform, heptane, TFT (trifluorotoluene), MeCN, and any combination or two or more thereof. In any embodiments, the reaction mixture from step (b) is extracted with butyl acetate.

In any embodiments, the extraction (e.g., step (c)) is a continuous extraction (e.g., occurs continuously by using in-line extractions). In any embodiments, the extraction (e.g., step (c)) is not a continuous extraction (e.g., occurs by using a separatory funnel).

In any embodiments, the process described herein may include a step (d), wherein the crude product (e.g. a potassium salt of the compound of Formula (A)) may be purified and isolated.

Steps (e) and (f)

In any embodiments, the process described herein may include a step (e), wherein a salt (e.g., a potassium salt) of the compound of Formula (A) is converted to its freebase form. In any embodiments, a salt (e.g., a potassium salt) of the compound of Formula (A) may be isolated and purified prior to step (e). In any embodiments, the salt (e.g., a potassium salt) of the compound of Formula (A) may be obtained from step (c) or step (d).

For example, a salt (e.g., a potassium salt) of the compound of Formula (A) can be converted to the corresponding freebase by reacting with an acid. Exemplary acids includes HCl (e.g., concentrated HCl), $H_2SO_4$, $HNO_3$, and any combination of two or more thereof. In any embodiments, the acid is concentrated HCl.

In any embodiments, step (e) occurs at a temperature of about 20° C. to 45° C. In any embodiments, step (e) occur at a temperature of at least about 20° C. to 45° C. In any embodiments, step (e) occur at a temperature of no more than about 20° C. to 45° C. In any embodiments, step (e) occur at a temperature of about 20° C. to 45° C., about 30° C. to 45° C., or about 35° C. to 45° C. In any embodiments, step (e) occur at a temperature of about 20° C., about ° C., about 30° C., about 35° C., about 40° C., or about 45° C. In any embodiments, step (e) occur at a temperature of about 25° C.

In any embodiments, the process described herein may include a step (f), wherein the crude product (e.g. a compound of Formula (A)) may be purified and isolated.

Step (g)

In any embodiments, methods described herein may include a step (g). In any embodiments, a compound of Formula (B) can be prepared according to Scheme 3.

Scheme 3 Exemplary Step (g)

i.

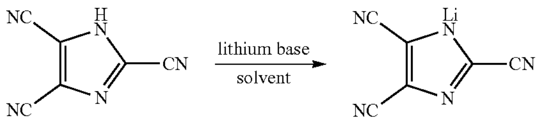

(A) (B)

ii.

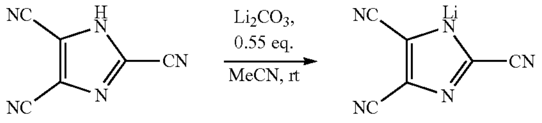

(A) (B)

As shown in Scheme 3-i, a step (g) can comprise reacting a compound of Formula (A) with a lithium base to form a compound of Formula (B). A further exemplary embodiment of a step (a) is shown in Scheme 3-ii. In any embodiments, a compound of Formula (A) is isolated and purified prior to step (g). In any embodiments, a compound of Formula (A) is obtained from step (e) or step (f).

In any embodiments, step (g) comprises reacting a compound of Formula (A) with a lithium base. Exemplary lithium base includes but is not limited to LiOH and $Li_2CO_3$. In any embodiments, the lithium base is $Li_2CO_3$. In any embodiments, In any embodiments, step (g) comprises reacting about 1 equivalent of compound of Formula (A) with about 0.5 to 2 equivalents of lithium base (e.g., $Li_2CO_3$). In any embodiments, In any embodiments, step (g) comprises reacting about 1 equivalent of compound of Formula (A) with at least about 0.5 to 2 equivalents of lithium base (e.g., $Li_2CO_3$). In any embodiments, In any embodiments, step (g) comprises reacting about 1 equivalent of compound of Formula (A) with no more than about 0.5 to 2 equivalents of lithium base (e.g., $Li_2CO_3$). In any embodiments, In any embodiments, step (g) comprises reacting about 1 equivalent of compound of Formula (A) with about 0.5 to 2 equivalents, about 0.5 to 1.5 equivalents, or about 0.5 to 1 equivalents of lithium base (e.g., $Li_2CO_3$). In any embodiments, step (g) comprises reacting about 1 equivalent of compound of Formula (A) with about 0.5, 0.7, 1, 1.2, 1.5, 1.7, or 2 equivalents of lithium base (e.g., $Li_2CO_3$).

In any embodiments, a compound of Formula (A) reacts with a lithium base in a solvent (e.g., MeCN solvent) in step (g).

In any embodiments, step (g) occurs at a temperature of about 20° C. to 45° C. In any embodiments, step (g) occurs at a temperature of at least about 20° C. to 45° C. In any embodiments, step (g) occur at a temperature of no more than about 20° C. to 45° C. In any embodiments, step (g) occur at a temperature of about 20° C. to 45° C., about 30° C. to 45° C., or about 35° C. to 45° C. In any embodiments, step (g) occur at a temperature of about 20° C., about ° C., about 30° C., about 35° C., about 40° C., or about 45° C. In any embodiments, step (g) occurs at a temperature of about 25° C.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with invention as defined in the claims which follow. The invention disclosed herein is further illustrated by the following examples which in no way should be construed as being limiting.

EXAMPLES

General Methods. Reagents were obtained from the following sources and used without further purification. Unless otherwise noted, all materials are reagent grade. 2-amino-4,5-dicyanoimidazole (TCI); acetonitrile (J. T. Baker); dimethylsulfoxide (VWR); tert-butyl nitrite (BTC or Sigma-Aldrich, technical grade, 90%); butyl acetate (Sigma-Aldrich); potassium cyanide (Acros); copper(I) cyanide (Alfa Aesar or Strem Chemicals); potassium carbonate (VWR). Other solvents are from Sigma-Aldrich.

Analysis was conducted on an Agilent 1100 HPLC instrument using gradient elution program. Column: Agilent eclipse Plus C18 3.5 μm, 100×4.6 mm. Program: 10% MeCN/water to 95% MeCN/water over 10 minutes, then to 100% MeCN over 2 minutes. Hold at 100% MeCN for 3 minutes. Observe at 254 nm.

Flow reactors are composed of various lengths and diameters of inert plastic tubing (e.g., PTFE, ETFE). Reagent solutions are introduced with syringe pumps, infusion/withdrawal syringe pumps, or HPLC pumps.

Example 1—Initial Screening

Examination of Aging Time of Diazonium Solution

Representative procedures: Aliquots of a solution prepared from amino-DCI (compound of Formula (I), 2-amino-1H-imidazole-4,5-dicarbonitrile) and t-Bu-ONO in MeCN/DMSO/water were allowed to age before dropwise addition to a solution of KCN and CuCN in water. No significant change in HPLC area was noted. Results are summarized in Table 1. Some dependence on the volume of water used in the KCN/CuCN solution was noted as a lighter solution color-lighter than expected simply based on dilution. Diazonium salt appears stable in solution.

TABLE 1

| No. | $H_2O$, mL | KCN, equiv | CuCN, equiv | Temperature, ° C. | Delay, min | HPLC purity, % |
|---|---|---|---|---|---|---|
| 1 | 2 | 1.4 | 0.4 | 20 | 10 | 77.33 |
| 2 | 2 | 1.4 | 0.4 | 20 | 30 | 78.55 |
| 3 | 2 | 1.4 | 0.4 | 20 | 60 | 76.25 |
| 4 | 4 | 1.4 | 0.4 | 20 | 360 | 76.58 |
| 5 | 6 | 1.4 | 0.4 | 20 | 1440 | 73.31 |

TABLE 1-continued

| No. | $H_2O$, mL | KCN, equiv | CuCN, equiv | Temperature, ° C. | Delay, min | HPLC purity, % |
|---|---|---|---|---|---|---|
| 6 | 8 | 1.4 | 0.4 | 20 | 1440 | 79.48 |
| 7 | 6 | 1.4 | 0.4 | 20 | 1440 | 78.19 |

Effect of K Equivalents

Representative procedures: Solution A ($DCI-NH_2$ (compound of Formula (I), 2-amino-1H-imidazole-4,5-dicarbonitrile) in MeCN/DMSO/water) and solution B (tert-butyl nitrite, t-Bu-ONO in MeCN) were pumped into a 3 ml tube coil using a tee-mixer at a rate to give a 10 minute residence time. The coil was placed into a room temperature (19-21° C.) water bath. The outlet tube was immersed in a solution of KCN and CuCN in water, under a strong nitrogen purge to remove any air. The quench solution was rapidly stirred (900 rpm) with magnetic stirring. The amount of KCN was varied. Results are summarized in Table 2. It appears that above a minimum threshold, there is minimum benefit to added KCN.

TABLE 2

| No. | compound of Formula (I), g | t-BuONO | $H_2O$, mL | KCN, equiv | CuCN, equiv | HPLC purity, % |
|---|---|---|---|---|---|---|
| 1 | 2.0077 | 2.5 ml | 30 | 1.80 | 0.55 | 78 |
| 2 | 1.9970 | 2.5 ml | 30 | 1.00 | 0.55 | 63.9 |
| 3 | 2.0148 | 2.5 ml | 25 | 1.39 | 0.55 | 80.5 |

Solvent Screening

Samples of $DCI-NH_2$ (40 mg) were slurried in acetonitrile (0.25 ml) plus various solvents (0.05 ml). Results such as solubility are summarized in Table 3.

TABLE 3

| No. | Solvent | Solubility | +100 uL solvent | +200 uL water |
|---|---|---|---|---|
| 1 | Sulfolane | No | No | soluble |
| 2 | Propylene carbonate | No | No | soluble |
| 3 | NMP | partial soluble | soluble | N/A |
| 4 | Nitromethane | No | No | No |
| 5 | Dmso | soluble | N/A | N/A |
| 6 | Diglyme | soluble | N/A | N/A |
| 7 | MeCN:water = 0.5:0.2 mL | soluble | N/A | N/A |

$DCI-NH_2$ samples (40 mg) were dissolved in various solvent systems. t-Bu-ONO (40 uL) was added and the HPLC analysis was taken (HPLC purity A). A solution of KCN/CuCN in water (1.5/0.7 equiv, 1 mL) was added to each vial and HPLC analysis was taken (HPLC purity B). The final HPLC analysis (HPLC purity C) was taken after overnight stirring. Results are summarized in Table 4.

TABLE 4

| No. | Solvent | HPLC purity A, % | HPLC purity B, % | HPLC purity C, % |
|---|---|---|---|---|
| 1 | Diglyme 400 uL | 71 | 10.4 | 0.4 |
| 2 | MeCN:$H_2O$:DMF = 300:100:50 | 93 | 61 | 62 |
| 3 | MeCN:DMSO = 300:100 | 88 | 63 | 65 |
| 4 | MeCN:NMP = 300:100 | 85 | 31 | 31 |

TABLE 4-continued

| No. | Solvent | HPLC purity A, % | HPLC purity B, % | HPLC purity C, % |
|---|---|---|---|---|
| 5 | MeCN:DMSO:$H_2O$ = 200:100:100 | 86 | 59 | 60 |
| 6 | MeCN:DMSO:$H_2O$ = 300:50:50 | 94 | 69 | 70 |
| 7 | MeCN:$H_2O$:DMF = 300:70:70 | 94 | 57 | 58 |

$DCI-NH_2$ samples (40 mg) were dissolved in various solvent systems. t-Bu-ONO (40 uL) was added and stirred for 10 minutes. The solution was added to a solution of KCN/CuCN in water (1.5/0.7 equiv, 1 mL) and HPLC analysis was taken. The final HPLC analysis was taken after overnight stirring. Results are summarized in Table 5.

TABLE 5

| No. | Solvent | HPLC purity, % |
|---|---|---|
| 1 | MeCN:$H_2O$:DMF = 300:100:50 | 62 |
| 2 | MeCN:DMSO = 300:100 | 63 |
| 3 | MeCN:DMSO:$H_2O$ = 200:100:100 | 56 |
| 4 | MeCN:DMSO:$H_2O$ = 300:50:50 | 65 |
| 5 | MeCN:$H_2O$:DMF = 300:70:70 | 62 |

Equivalents Screening

Amino-dicyanoimidazole (0.4001 g) was dissolved in MeCN:DMSO:water (3000:500:500 ul) and stirred to dissolve. $^t$Bu-ONO (450 ul, 1.25 eq) was added and stirred for 20 minutes (HPLC 98.9%). 400 uL aliquots were added to KCN/CuCN solutions in a room temperature water bath. Results are summarized in Table 6.

TABLE 6

| No. | $H_2O$, mL | KCN, equiv. | CuCN, equiv. | HPLC purity, % |
|---|---|---|---|---|
| 1 | 0.5 | 1.56 | 0.21 | 59.4 |
| 2 | 0.5 | 1.50 | 0.38 | 74.1 |
| 3 | 0.5 | 1.52 | 0.50 | 74.2 |
| 4 | 0.5 | 1.51 | 0.58 | 72.4 |
| 5 | 0.5 | 1.52 | 0.80 | 64.4 |
| 6 | 0.5 | 0.81 | 0.42 | 67.6 |
| 7 | 0.5 | 1.11 | 0.38 | 76 |
| 8 | 0.5 | 1.23 | 0.38 | 74.4 |
| 9 | 0.5 | 1.41 | 0.39 | 72.5 |
| 10 | 0.5 | 1.60 | 0.40 | 69.8 |

Temperature Screening

Thermostat 20° C.: Amino-dicyanoimidazole (0.4014 g) was dissolved in MeCN:DMSO:water (3000:500:500 ul) and stirred to dissolve. tBu-ONO (450 ul) was added and stirred for 30 minutes. This solution was then injected (syringe pump, 0.5 ml/min) into a 1 ml PTFE flow coil in a 20° C. water bath with a solution of KCN (0.2365 g), CuCN (0.1061 g) in water (4.5 ml) via a tee-mixer. Three aliquots were taken—first 2 ml, second 2 ml and the remainder. HPLC results: 71.6, 72.6, 73.5, showing essentially no change over time.

Thermostat 38° C.: Amino-dicyanoimidazole (0.4017 g) was dissolved in MeCN:DMSO:water (3000:500:500 ul) and stirred to dissolve. tBu-ONO (450 ul) was added and stirred for 30 minutes. This solution was then injected (syringe pump, 0.5 ml/min) into a 1 ml PTFE flow coil in a 38° C. water bath with a solution of KCN (0.2338 g), CuCN (0.1076 g) in water (4.5 ml) via a tee-mixer. Three aliquots were taken—first 2 ml, second 2 ml and the remainder. HPLC results: 72.0, 70.6, 72.2, showing essentially no change over time.

Thermostat 0° C.: Amino-dicyanoimidazole (0.4020 g) was dissolved in MeCN:DMSO:water (3000:500:500 ul) and stirred to dissolve. tBu-ONO (450 ul) was added and stirred for 30 minutes. This solution was then injected (syringe pump, 0.5 ml/min) into a 1 ml PTFE flow coil in an ice water (0° C.) bath with a solution of KCN (0.2350 g), CuCN (0.1046 g) in water (4.5 ml) via a tee-mixer. The mixture plugged the coil and the experiment was not completed.

Example 2—Flow Chemistry Screening

Examination of KCN and CuCN Equivalents.

Representative procedure: Amino-dicyanoimidazole (e.g., 2.0148 g) was dissolved in MeCN:DMSO:water (15.0:2.5:2.5 ml) and stirred to dissolve to make solution A. tBu-ONO (2.5 ml) was dissolved in acetonitrile (6.5 ml) to make solution B. Solutions A and B were injected (syringe pump, 12.6 ml/h and 5.4 ml/h) into a 3 ml PTFE flow coil, targeting 10 min residence time. Upon exiting, the reaction mixture was quenched into a stirred solution of KCN (various, see table) and CuCN (various, see table) in water (25 ml), under a strong nitrogen purge. Results are summarized in Table 7.

TABLE 7

| No. | amin-DCI, g | $H_2O$, mL | KCN, equiv. | CuCN, equiv. | Temperature, ° C. | Delay, min | HPLC purity, % |
|---|---|---|---|---|---|---|---|
| 1 | 2.0077 | 30 | 1.80 | 0.55 | 20 | 10 | 78 |
| 2 | 1.997 | 30 | 1.00 | 0.55 | 20 | 10 | 63.9 |
| 3 | 2.0148 | 25 | 1.39 | 0.55 | 20 | 10 | 80.5 |
| 4 | 2.0013 | 25 | 1.40 | 0.27 | 20 | 10 | 67.7 |
| 5 | 1.999 | 25 | 1.41 | 0.53 | 20 | 10 | 73.91 |
| 6 | 1.9996 | 25 | 1.40 | 0.82 | 20 | 10 | 66.15 |

Examination on Diazonium Stability

Amino-dicyanoimidazole (0.5005 g) was dissolved in MeCN:DMSO:water (3.0:0.7:0.7 ml) and stirred to dissolve. tBu-ONO (0.63 ml) was added and a timer was started. At the specified time in the table, a 1.0 ml aliquot was removed and quenched into a vial containing KCN and CuCN. HPLC analysis was run as soon as possible. HPLC showed basically unchanged results over time, showing the solution is stable. Results are summarized in Table 8.

TABLE 8

| No. | amino-DCI | $H_2O$, mL | KCN, equiv. | CuCN, equiv. | Temperature, ° C. | Delay, min | HPLC purity, % |
|---|---|---|---|---|---|---|---|
| 1 | 0.5005 (aliquots taken) | 2 | 2.60 | 1.04 | 20 | 10 | 77.33 |
| 2 | As above | 2 | 2.63 | 1.06 | 20 | 30 | 78.55 |
| 3 | As above | 2 | 2.65 | 1.07 | 20 | 60 | 76.25 |
| 4 | As above | 4 | 2.62 | 1.00 | 20 | 360 | 76.58 |
| 5 | As above | 6 | 2.77 | 1.02 | 20 | 1440 | 73.31 |
| 6 | As above | 8 | 2.64 | 1.02 | 20 | 1440 | 79.48 |
| 7 | As above | 6 | 2.71 | 1.33 | 20 | 1440 | 78.19 |

Examination on Workup Conditions

A solution of KCN/CuCN (0.3679 g, 0.1452 g) in water (8 ml) was prepared and split into 1 mL aliquots. A previously prepared solution of the 4,5-dicyano-1H-imidazole-2-diazonium intermediate was then added to each with the following modifications: added base, added solvent (2 mL dichloromethane) and/or run under air instead of nitrogen atmosphere. Results are summarized in Table 9.

TABLE 9

| No. | $K_2CO_3$ | DCM | Air | Color | HPLC purity, % |
|---|---|---|---|---|---|
| 1 | Y | Y | Y | red | 87.5 |
| 2 | Y | Y | N | red | 90.0 |
| 3 | Y | N | Y | red | 80.3 |
| 4 | N | Y | Y | green-brown | 85.0 |
| 5 | Y | N | N | red | 80.4 |
| 6 | N | Y | N | green-brown | 86.9 |
| 7 | N | N | Y | green-brown | 76.9 |
| 8 | N | N | N | green-brown | 77.7 |

Temperature and Residence Time Screen

Representative procedure: Amino-dicyanoimidazole (2.0024 g) was dissolved in MeCN:DMSO:water (15.0:2.5:2.5 ml) and stirred to dissolve to make solution A. tBu-ONO (1.83 g) was dissolved in acetonitrile to make 9.0 ml of solution B. Solutions A and B were injected (syringe pump, 12.6 ml/h and 5.4 ml/h) into a 3 ml PTFE flow coil, targeting 10 min residence time in a 20° C. water bath. Upon exiting, the reaction mixture was quenched into a stirred solution of KCN (1.3701 g), CuCN (0.5205 g) and $K_2CO_3$ (2.1884 g) in water (30 ml) and dichloromethane (10 ml). Nitrogen was bubbled through the solution. Results are summarized in Table 10.

TABLE 10

| No. | amin-DCI, g | $H_2O$, mL | KCN, equiv. | CuCN, equiv. | $K_2CO_3$, equiv. | Temperature, ° C. | Delay, min | HPLC purity, % |
|---|---|---|---|---|---|---|---|---|
| 1 | 2.0024 | 30 | 1.40 | 0.53 | 1.05 | 20 | 10 | 82.1 |
| 2 | 1.9979 | 20 | 1.41 | 0.55 | 1.06 | 20 | 10 | 77.48 |
| 3 | 1.9977 | 20 | 1.41 | 0.55 | 1.01 | 30 | 10 | 86.54 |
| 4 | 2.001 | 20 | 1.40 | 0.55 | 1.01 | 40 | 5 | 85.28 |
| 5 | 1.9989 | 20 | 1.39 | 0.58 | 1.07 | 40 | 5 | 68 |
| 6 | 0.0992 | 2 | 1.38 | 0.53 | 1.02 | 20 | 20 | 55 |
| 7 | 0.0992 | 2 | 1.40 | 0.57 | 1.06 | 20 | 20 | 78.3 |
| 8 | 0.0992 | 2 | 1.42 | 0.59 | 1.14 | 20 | 20 | 75.6 |

Optimization Runs

Representative procedure: Amino-dicyanoimidazole (2.0033 g) was dissolved in MeCN:DMSO:water (15.0:2.5:2.5 ml) and stirred to dissolve to make solution A. tBu-ONO (1.83 g) was dissolved in MTBE or other solvent listed in the table to make 10.0 ml of solution B. Solutions A and B were injected (syringe pump, 24.4 ml/h and 11.6 ml/h) into a 3 ml PTFE flow coil, targeting 5 min residence time in a 45° C. water bath. In experiments No. 1-6, this flow stream was mixed with a third stream consisting of KCN (1.3762 g), CuCN (0.5405 g) and $K_2CO_3$ (2.1207 g) in water (total 31 ml volume), pumped at a rate of 36 ml/min. This exited the system into a collection flask containing more solvent (MTBE) that was kept under a slow nitrogen purge. In experiments No. 7-12, the reaction mixture was quenched into a stirred solution of KCN, CuCN, and $K_2CO_3$ in water (30 ml) and solvent (10 ml). Nitrogen was bubbled through the solution. HPLC data were recorded. Results are summarized in Table 11.

TABLE 11

| No. | DCI-$NH_2$, g | $BuNO_2$, g | KCN, g | CuCN, g | $K_2CO_3$, g | Co-solvent | Temp, ° C. | Ret, min | wt, isolated product, g | Yield, % | color | HPLC purity (aqueous phase), % | HPLC purity (organic phase), % | % in organic phase |
|---|---|---|---|---|---|---|---|---|---|---|---|---|---|---|
| 1 | 2.0033 | 1.83 | 1.3762 | 0.5405 | 2.1207 | MTBE | 45 | 5 | | | | 54.67 | 89.64 | 48.44268 |
| 2 | 2.0023 | 1.85 | 1.3779 | 0.539 | 2.0822 | toluene | 45 | 5 | | | | 80 | 70 | 0.397753 |
| 3 | 1.9986 | 1.91 | 1.3752 | 0.5316 | 2.0903 | TFT | 45 | 5 | | | | 83 | 80 | 6.278566 |
| 4 | 2.0006 | 1.88 | 1.3768 | 0.5347 | 2.0861 | DCM | 35 | 5 | | | | 88 | 99 | 13.90955 |
| 5 | 1.9942 | 1.91 | 1.3624 | 0.5306 | 2.0603 | MeCN | 35 | 5 | | | | 73.61 | | |
| 6 | 1.9935 | 1.88 | 1.3714 | 0.542 | 2.1375 | BuOAc | 35 | 5 | | | | 66.94 | 93.1 | 52.84931 |
| 6 2× | | | | | | BuOAc | | | | | | 47.34 | 99.08 | 48.15177 |
| 7 | 1.9981 | 2.01 | 1.3822 | 0.5381 | 2.0821 | TFT | 40 | 5 | 1.80 | 66.11 | yellow | 90.4 | 92.3 | 5.212995 |
| 8 | 1.9908 | 1.97 | 1.3689 | 0.5352 | 2.0868 | DCM | 40 | 5 | 1.66 | 60.97 | yellow | 89.85 | 98.2 | 20.00143 |
| 9 | 2.0114 | 1.94 | 1.3817 | 0.5364 | 2.085 | toluene | 40 | 5 | 1.35 | 49.58 | gold | 81.97 | 89 | 1.654801 |
| 10 | 2.0029 | 1.96 | 1.3706 | 0.5322 | 2.1397 | MeCN | 40 | 5 | 1.36 | 49.95 | gold | 78.4 | | |
| 11 | 1.9968 | 1.94 | 1.3747 | 0.5311 | 2.1025 | MTBE | 40 | 5 | 1.30 | 47.75 | red | 63.74 | 92.814 | 56.28386 |
| 11 2× | | | | | | | | | | | | 60.06 | 97.3 | 15.63757 |
| 11 3× | | | | | | | | | | | | | 100 | |
| 11 4× | | | | | | | | | | | | | 96.89 | |
| 12 | 2.0031 | 1.96 | 1.4038 | 0.5407 | 2.1065 | BuOAc | 40 | 5 | 1.59 | 58.40 | red | 63.5 | 97.44 | 56.07404 |
| 12 2× | | | | | | | | | | | | 39.1 | 97.13 | 57.99806 |
| 12 3× | | | | | | | | | | | | 1.85 | 92.52 | 93.64359 |

Example 3—Scale Up Preparation

Full-continuous and semi-continuous preparation of compound of Formula (A) or a salt thereof—formation of potassium salt of compound of Formula (A) (K-TCI).

Amino-dicyanoimidazole (50.24 g) was dissolved in MeCN:DMSO:water (375:62:62 ml, total 550 ml) and stirred to dissolve to make solution A. $^t$Bu-ONO (45.42 g) was dissolved in BuOAc to make a total of 550 ml of solution B. Solutions A and B were injected (HPLC pumps) into a flow coil of 21 ml volume immersed in a water bath at 40° C. The residence time is 5 or 7 minutes. In a semi-continuous method, this solution was then quenched into a solution of KCN (34.35 g), CuCN (13.48 g) and $K_2CO_3$ (52.08 g) in water (650 ml). In a full-continuous method, this flow stream was mixed with a third stream consisting of KCN, CuCN and $K_2CO_3$ in water. This exited the system into a tube reactor to allow mixing and nitrogen gas evolution and separation, then into collection flask containing more solvent (BuOAc) that was kept under a slow nitrogen purge.

The final solution was collected and extracted with BuOAc several times to remove the K-TCI from the other inorganic salts. The organic extracts were concentrated on the rotovap to give an orange-red to brown solid. Results obtained under various conditions are summarized in Table 12.

TABLE 12

| No. | DCI-$NH_2$, g | $BuNO_2$, g | KCN, g | CuCN, g | $K_2CO_3$, g | Co-solvent | KCN, equiv. | CuCN, equiv. | $K_2CO_3$, equiv. | Temp, ° C. | Delay, min | isolated weight, g | HPLC purity in organic phase, % | Note |
|---|---|---|---|---|---|---|---|---|---|---|---|---|---|---|
| 1 | 50.24 | 45.42 | 34.35 | 13.48 | 52.08 | BuOAc | 1.40 | 0.55 | 1.00 | 40 | 5 | 38.47 | 94.04 | semi |
| 2 | 70.01 | 66.20 | 47.98 | 18.89 | 73.27 | BuOAc | 1.40 | 0.55 | 1.0 | 40 | 5 | 49.15 | 91.3 | semi |
| 3 | 70.09 | 63.62 | 47.96 | 18.86 | 73.02 | BuOAc | 1.40 | 0.55 | 1.00 | 36 | 7 | 62.43 | 92 | semi |
| 4 | 50.00 | 45.92 | 32.32 | 13.46 | 42.48 | BuOAc | 1.32 | 0.55 | 0.82 | 36 | 7 | 45.04 | 99 | semi |
| 5[a] | 50.03 | 46.23 | 34.26 | 13.48 | 52.00 | BuOAc | 1.40 | 0.55 | 1.00 | 35 | 7 | 50.21 | 97.51 | full |
| 6 | 50.02 | 45.95 | 34.26 | 13.46 | 52.20 | BuOAc | 1.40 | 0.55 | 1.01 | 35 | 7 | spill | 95.1 | full |
| 7[b] | 50.00 | 50.66 | 34.26 | 13.47 | 52.14 | BuOAc | 1.400598 | 0.550673 | 1.00432 | 35 | 7 | 58.78 | 92.05 | full |
| 8[c] | 50.02 | 46.94 | 34.35 | 13.49 | 52.81 | BuOAc | 1.40 | 0.55 | 1.02 | 25 | 7 | 44.98 | 95.13 | full |
| 9[c] | 50.02 | 50.05 | 34.30 | 13.50 | 51.98 | BuOAc | 1.40 | 0.55 | 1.00 | 37 | 7 | 61.33 | 97.69 | full |
| 10[c] | 25.02 | 23.73 | 17.25 | 6.75 | 26.25 | BuOAc | 1.409283 | 0.551458 | 1.010446 | 35 | 7 | 21.74 | 97.88 | full |
| 11[c] | 25.02 | 23.67 | 17.21 | 6.83 | 29.00 | BuOAc | 1.406015 | 0.557994 | 1.116303 | 35 | 7 | 24.08 | 91.01 | full |
| 12 | 25.05 | 21.29 | 17.30 | 6.74 | 26.17 | BuOAc | 1.411675 | 0.549982 | 1.00616 | 37 | 7 | 19.50 | 94.69 | full |
| 13 | 25.08 | 23.60 | 17.31 | 6.75 | 38.35 | BuOAc | 1.410801 | 0.550139 | 1.472682 | 35 | 7 | 20.69 | 91.85 | full |

[a]Added reaction tube;

[b]Tilted reaction tube;

[c]Added membrane separator.

Wash Steps—Purification

Combined organic extracts were dried and re-dissolved in 3:2 BuOAc:MeCN. These solutions were washed with conc $K_2CO_3$(aq); saturated NaCl (aq), and water. Only water extracted any material with color, although by HPLC, considerable product is lost.

Formation of Freebase Form—Compound of Formula (A) (H-TCI)

Solid K-TCI (150.10 g) was added to a 1 L Erlenmeyer flask and slurried in water (600 ml) and washed with MTBE (200 ml). The solvent was removed fresh MTBE was added. The mixture was acidified with concentrated HCl. Layers were separated and the aqueous layer extracted again. Combined organic layers were treated with 20 g of activated carbon (DARCO). The solids were removed by filtration and the solution re-treated. No noticeable effect was observed. The solution was rotovaped to a red oil which was re-dissolved in water (450 ml), and treated three times with DARCO to give a pale yellow solution. This was extracted into MTBE, dried and rotovaped to a yellow oil (69.8 g, 58.9% yield).

Formation of Lithium Salt of Compound of Formula (A) (Li-TCI).

The H-TCI (69 g) was dissolved in acetonitrile (500 ml) and treated with lithium carbonate (19.6 g). Some foaming occurred. The suspension was stirred overnight, then DARCO (10 g) was added. The suspension was filtered through a Celite pad after 10 minutes of stirring to give a clear yellow solution. The solution was dried on the rotovap. The solids were sonocated in 1 L MTBE for 45 minutes and then stirred overnight. Filtration and washing with MTBE gave an off-white solid. (97% HPLC).

Further Embodiments of the Present Technology

The present technology also includes at least the following additional embodiments:

In embodiment 1, there is provided a continuous process for preparing a compound of Formula (A)

(A)

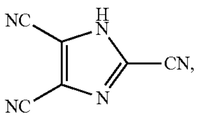

or a salt thereof, comprising:

(a) contacting a first reaction stream comprising a compound of Formula (I)

(I)

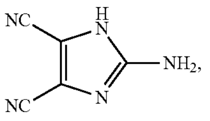

with a second reaction stream comprising a nitrite source, to form a first combined reaction stream comprising a compound of Formula (II)

(II)

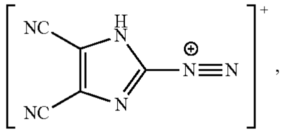

or a tautomer thereof, wherein the first combined reaction stream flows through a continuous flow reactor at a flow rate providing a residence time sufficient for converting a compound of Formula (I) to a compound of Formula (II); and (b) a step selected from step (b1) and (b2), wherein step (b1) comprises contacting the first combined reaction stream with a third reaction stream comprising a cyanide source to form a second combined reaction stream to form a compound of Formula (A) or a salt thereof, wherein the second combined reaction stream is allowed to flow through a continuous flow reactor; and step (b2) comprises quenching the reactor effluent exiting from the continuous flow reactor with a cyanide source to form a quench mixture comprising compound of Formula (A) or a salt thereof.

Embodiment 2 provides a process of embodiment 1, wherein the nitrite source in step (a) is tert-butyl nitrite, amyl nitrite, sodium nitrite, or nitrous acid.

Embodiment 3 provides a process of embodiments 1 or 2, wherein the nitrite source in step (a) is tert-butyl nitrite.

Embodiment 4 provides a process of any one of embodiments 1-3, wherein the nitrite source is present in the first combined reaction stream in an amount of about 70 to 150 mol % relative to the compound of Formula (I).

Embodiment 5 provides a process of any one of embodiments 1-4, wherein the nitrite source is present in the first combined reaction stream in an amount of about 120 mol % relative to the compound of Formula (I).

Embodiment 6 provides a process of any one of embodiments 1-5, wherein the first reaction stream and/or the second reaction stream in step (a) comprise a solvent.

Embodiment 7 provides a process of embodiment 4, wherein the solvent comprises DMSO, Diglyme, MeCN, $H_2O$, DMF, NMP, BuOAc, or any combination of two or more thereof.

Embodiment 8 provides a process of embodiments 4 or 7, wherein the first reaction stream solvent comprises a combination of MeCN, DMSO, and water.

Embodiment 9 provides a process of embodiment 8, wherein MeCN, DMSO, and water are present in the solvent combination in an amount ranging from about 30% to 80%, from about 10% to 30%, and from about 10% to 30%, respectively.

Embodiment 10 provides a process of embodiments 8 or 9, wherein MeCN, DMSO, and water are present in a ratio of 6:1:1.

Embodiment 11 provides a process of embodiments 6 or 7, wherein the second reaction stream comprises the solvent BuOAc.

Embodiment 12 provides a process of any one of embodiments 1-11, wherein step (b) is step (b1), and wherein the third reaction stream in step (b1) comprises a solvent.

Embodiment 13 provides a process of any one of embodiments 1-11, wherein step (b) is step (b2), and wherein the cyanide source is dissolved in a solvent prior to step (b2).

Embodiment 14 provides a process of embodiments 12 or 13, wherein the solvent is water.

Embodiment 15 provides a process of any one of embodiments 1-14, wherein the cyanide source is an inorganic cyanide salt.

Embodiment 16 provides a process of embodiment 15, wherein the cyanide source is CuCN, KCN, NaCN, or $Zn(CN)_2$.

Embodiment 17 provides a process of embodiments 15 or 16, wherein the cyanide source is present in the second combined reaction stream or the quench mixture in an amount of about 100 to 300 mol % relative to the compound of Formula (II).

Embodiment 18 provides a process of embodiments 15 or 16, wherein the cyanide source is a combination of KCN and CuCN.

Embodiment 19 provides a process of embodiment 1814, wherein the KCN is present in the second combined reaction stream or the quench mixture in an amount of about 50 to 200 mol % relative to the compound of Formula (II); and CuCN is present in the second combined reaction stream or the quench mixture in an amount of about 20 to 100 mol % relative to the compound of Formula (II).

Embodiment 20 provides a process of embodiments 18 or 19, wherein the KCN is present in the second combined reaction stream or the quench mixture in an amount of about 140 mol % relative to the compound of Formula (II); and CuCN is present in the second combined reaction stream or the quench mixture in an amount of about 55 mol % relative to the compound of Formula (II).

Embodiment 21 provides a process of any one of embodiments 1-20, wherein the second combined reaction stream in step (b1) or the quench mixture in step (b2) further comprises a base.

Embodiment 22 provides a process of embodiment 21, wherein the base is an inorganic base.

Embodiment 23 provides a process of any embodiments 21 or 22, wherein the inorganic base is LiOH, NaOH, KOH, CsOH, $Li_2CO_3$, $Na_2CO_3$, $K_2CO_3$, $Cs_2CO_3$, $NaHCO_3$, $KHCO_3$, $CsHCO_3$, or any combination of two or more thereof.

Embodiment 24 provides a process of embodiment 23, wherein the base is $K_2CO_3$.

Embodiment 25 provides a process of any one of embodiments 21-24, wherein the base is present in the second combined reaction stream or the quench mixture in an amount of about 100 to 300 mol % relative to the compound of Formula (II).

Embodiment 26 provides a process of any one of embodiments 21-24, wherein the base is present in the second combined reaction stream or the quench mixture in an amount of about 100 mol % relative to the compound of Formula (II).

Embodiment 27 provides a process of any one of embodiments 1-26, wherein step (a), step (b1), and/or step (b2) occur at a temperature of about 20° C. to about 45° C.

Embodiment 28 provides a process of embodiment 27, wherein step (a) occur at a temperature of about 40° C.

Embodiment 29 provides a process of embodiment 27, wherein step (b1) and/or step (b2) occur at a temperature of about 25° C.

Embodiment 30 provides a process of any one of embodiments 1-30, wherein the flow rate provides a residence time in the range of about 5 minutes to about 24 hours.

Embodiment 31 provides a process of embodiment 30, wherein the flow rate provides a residence time of 5 minutes to 7 minutes.

Embodiment 32 provides a process of any one of embodiments 1-31, wherein the process is operated at atmospheric pressure.

Embodiment 33 provides a process of any one of embodiments 1-31, wherein the process is operated at an elevated pressure.

Embodiment 34 provides a process of any embodiments 32 or 33, wherein the process is operated at a pressure of about 1 to 10 bar.

Embodiment 35 provides a process of any one of embodiments 1-34, wherein the first combined reaction stream and/or the second combined reaction stream is biphasic, or the quench mixture is biphasic.

Embodiment 36 provides a process of any one of embodiments 1-34, wherein the first combined reaction stream and/or the second combined reaction stream is multi-phasic, and the multi-phasic first combined reaction stream and/or second combined reaction stream each consists of an organic-water phase and an immiscible organic solvent.

Embodiment 37 provides a process of embodiment 36, wherein the immiscible organic solvent comprises butyl acetate, MTBE(methyl tert-butyl ether), toluene, dichloromethane, chloroform, heptane, TFT (trifluorotoluene), MeCN, or any combination of two or more thereof.

Embodiment 38 provides a process of any embodiments 36 or 37, wherein the immiscible organic solvent is butyl acetate.

Embodiment 39 provides a process of any one of embodiments 1-38, further comprising: (c*) optionally separating the phases of the second combined reaction stream continuously, wherein the second combined reaction stream is biphasic or multi-phasic.

Embodiment 40 provides a process of any one of embodiments 1-40, further comprising collecting a reactor effluent exiting from the continuous flow reactor.

Embodiment 41 provides a process of any one of embodiments 1-40, further comprising:

(c) extracting the reaction mixture from step (b1), step (b2) or step (c*) with an organic solvent; and (d) optionally purifying the product from step (c).

Embodiment 42 provides a process of embodiment 41, wherein the organic solvent is butyl acetate, MTBE(methyl tert-butyl ether), toluene, dichloromethane, chloroform, heptane, TFT (trifluorotoluene), MeCN, or any combination thereof.

Embodiment 43 provides a process of embodiments 41 or 42, wherein the organic solvent is butyl acetate.

Embodiment 44 provides a process of any one of embodiments 41-43, wherein the extraction occurs continuously.

Embodiment 45 provides a process of any one of embodiments 41-44, further comprising:

(e) converting a salt of the compound of Formula (A) to its freebase form by reacting it with an acid, wherein the salt of the compound of Formula (A) is obtained from step (c) or step (d); and (f) optionally purifying the freebase compound of Formula (A).

Embodiment 46 provides a process of embodiment 45, wherein the salt of compound of Formula (A) is a potassium salt of compound of Formula (A).

Embodiment 47 provides a process of embodiment 45, wherein the acid is HCl.

Embodiment 48 provides a process of any one of embodiments 1-47, further comprising (g) reacting a freebase compound of Formula (A) with a lithium base to form a compound of Formula (B),

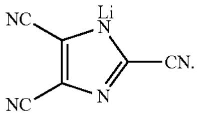

(B)

Embodiment 49 provides a process of any one of embodiment 48, wherein the lithium base is $Li_2CO_3$.

All references, patents or applications, U.S. or foreign, cited in the application are hereby incorporated by reference as if written herein in their entireties. Where any inconsistencies arise, material literally disclosed herein controls.

What is claimed is:

1. A continuous process for preparing a compound of Formula (A)

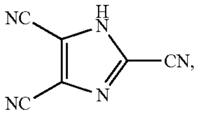

(A)

or a salt thereof, the process comprising:

(a) contacting a first reaction stream comprising a compound of Formula (I)

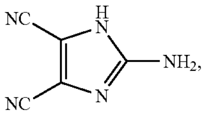

(I)

with a second reaction stream comprising a nitrite source, to form a first combined reaction stream comprising a compound of Formula (II)

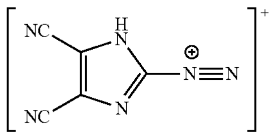

(II)

, or a tautomer thereof, wherein the first combined reaction stream flows through a continuous flow reactor at a flow rate providing a residence time sufficient for converting a compound of Formula (I) to a compound of Formula (II); and (b) a step selected from step (b1) and (b2), wherein step (b1) comprises contacting the first combined reaction stream further comprising an inorganic base with a third reaction stream comprising a cyanide source to form a second combined reaction stream to form a compound of Formula (A) or a salt thereof, wherein the second combined reaction stream is allowed to flow through a continuous flow reactor; and step (b2) comprises quenching the reactor effluent exiting from the continuous flow reactor with a cyanide source to form a quench mixture comprising compound of Formula (A) or a salt thereof and an inorganic base.

2. The process of claim 1, wherein the nitrite source in step (a) is tert-butyl nitrite, amyl nitrite, sodium nitrite, or nitrous acid.

3. The process of claim 1, wherein the nitrite source is present in the first combined reaction stream in an amount of about 70 to 150 mol % relative to the compound of Formula (I).

4. The process of claim 1, wherein the first reaction stream and/or the second reaction stream in step (a) comprise a solvent.

5. The process of claim 4, wherein the solvent comprises DMSO, Diglyme, MeCN, $H_2O$, DMF, NMP, BuOAc, or any combination of two or more thereof.

6. The process of claim 4, wherein the first reaction stream solvent comprises a combination of MeCN, DMSO, and water.

7. The process of claim 6, wherein MeCN, DMSO, and water are present in the solvent combination in an amount ranging from about 30% to 80%, from about 10% to 30%, and from about 10% to 30%, respectively.

8. The process of claim 4, wherein the second reaction stream comprises the solvent BuOAc.

9. The process of claim 1, wherein step (b) is step (b1), and wherein the third reaction stream in step (b1) comprises a solvent.

10. The process of claim 1, wherein step (b) is step (b2), and wherein the cyanide source is dissolved in a solvent prior to step (b2).

11. The process of claim 9, wherein the solvent is water.

12. The process of claim 1, wherein the cyanide source is CuCN, KCN, NaCN, or Zn(CN) 2.

13. The process of claim 12, wherein the cyanide source is present in the second combined reaction stream or the quench mixture in an amount of about 100 to 300 mol % relative to the compound of Formula (II).

14. The process of claim 1, wherein the cyanide source is a combination of KCN and CuCN.

15. The process of claim 14, wherein the KCN is present in the second combined reaction stream or the quench mixture in an amount of about 50 to 200 mol % relative to the compound of Formula (II); and CuCN is present in the second combined reaction stream or the quench mixture in an amount of about 20 to 100 mol % relative to the compound of Formula (II).

16. The process of claim 1, wherein the inorganic base comprises LiOH, NaOH, KOH, CsOH, $Li_2CO_3$, $Na_2CO_3$, $K_2CO_3$, $Cs_2CO_3$, $NaHCO_3$, $KHCO_3$, $CsHCO_3$, or any combination of two or more thereof.

17. The process of claim 1, wherein the inorganic base is present in the second combined reaction stream or the quench mixture in an amount of about 100 to 300 mol % relative to the compound of Formula (II).

18. The process of claim 1, wherein step (a), step (b1), and/or step (b2) occur at a temperature of about 20° C. to about 45° C.

19. The process of claim 1, wherein the process is operated at a pressure of about 1 to 10 bar.

20. A continuous process for preparing a compound of Formula (A)

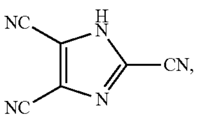

(A)

or a salt thereof, the process comprising:

(a) contacting a first reaction stream comprising a compound of Formula (I)

(I)

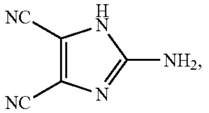

with a second reaction stream comprising a nitrite source, to form a first combined reaction stream comprising a compound of Formula (II)

(II)

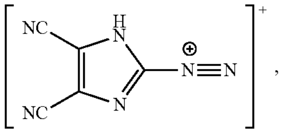

or a tautomer thereof, wherein the first combined reaction stream flows through a continuous flow reactor at a flow rate providing a residence time sufficient for converting a compound of Formula (I) to a compound of Formula (II); and (b) a step selected from step (b1) and (b2), wherein:

step (b1) comprises contacting the first combined reaction stream with a third reaction stream comprising a cyanide source to form a second combined reaction stream to form a compound of Formula (A) or a salt thereof, wherein the second combined reaction stream is allowed to flow through a continuous flow reactor; and step (b2) comprises quenching the reactor effluent exiting from the continuous flow reactor with a cyanide source to form a quench mixture comprising compound of Formula (A) or a salt thereof; and the process is operated at a pressure of about 1 to 10 bar.

* * * * *